US00PP30748P2

(12) United States Plant Patent
Hansen

(10) Patent No.: US PP30,748 P2
(45) Date of Patent: Jul. 23, 2019

(54) ***HOSTA* PLANT NAMED 'ETCHED GLASS'**

(50) Latin Name: ***Hosta* hybrid (Tratt.)**
Varietal Denomination: Etched Glass

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/998,207

(22) Filed: Jul. 13, 2018

(51) Int. Cl.
*A01H 5/12* (2018.01)
*A01H 6/56* (2018.01)

(52) U.S. Cl.
USPC ..... Plt./353

(58) Field of Classification Search
USPC ..... Plt./353
See application file for complete search history.

*Primary Examiner* — Susan McCormick Ewoldt

(57) ABSTRACT

A new and distinct *Hosta* plant named 'Etched Glass' with compact rounded-mound habit of heavy-substance, cordate foliage having wavy margins, acute apex and cordate base with variegated dark green margins, light yellowish centers and intermediate melded colors between the margin and center. The plant has near white, lightly fragrant flowers densely arranged on chartreuse-colored scapes just above the foliage.

1 Drawing Sheet

Latin name and variety denomination of the plant:
Botanical classification: *Hosta* hybrid (Tratt.).
Variety denomination: 'Etched Glass'.

FEDERALLY SPONSORED RESEARCH

This invention was developed without any federally sponsored research or development funding.

BACKGROUND AND ORIGIN OF THE PLANT

The present invention relates to a new and distinct *hosta* plant, *Hosta* 'Etched Glass' hereinafter also referred to as the new plant or just the cultivar name, 'Etched Glass'. *Hosta* 'Etched Glass' was discovered by the inventor at a wholesale nursery in Zeeland, Mich., USA on Jul. 8, 2013 as a whole plant sport in a tissue culture propagated batch of plants of 'Stained Glass' (not patented). The new plant has been asexually propagated by division at the same nursery in Zeeland, Mich., USA since 2016 and also by careful plant shoot-tip tissue culture with the resultant asexually propagated plants having retained all the same traits as the original plant.

No plants of *Hosta* 'Etched Glass' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

BRIEF SUMMARY OF THE PLANT

There are over 5,800 registered *hosta* cultivars with The American *Hosta* Society, which is the International Cultivar Registration Authority for the genus *Hosta* along with a similar number of unregistered cultivars. The nearest known comparison cultivars are *Hosta* 'Stained Glass' (not patented), 'Cathedral Windows' U.S. Plant Pat. No. 17,295, 'Guacamole' (not patented), 'Emerald Charger' (not patented) and 'Holy Mole' (not patented).

'Etched Glass', 'Cathedral Windows' and 'Emerald Charger' are all sports of 'Stained Glass'. 'Stained Glass' and 'Holy Mole' are sports from 'Guacamole'. All of the above plants have a green margin and lighter variegated center and lightly fragrant flowers. 'Guacamole' has a narrow margin with a chartreuse center. 'Cathedral Windows' and 'Holy Mole' both have a broader margins with chartreuse centers. 'Stained Glass' has a narrow margin with a center that is lighter or more yellowish than 'Guacamole'. 'Etched Glass' has margins that are wider than all the above except 'Emerald Charger'. 'Etched Glass' and 'Emerald Charger' both have center variegation with a more yellowish and less chartreuse color than 'Guacamole'. 'Etched Glass' and 'Emerald Charger' both have leaves with greater substance that are stiffer than the other above comparison plants.

Other *Hosta* cultivars have variegated foliage, but 'Etched Glass' is distinct from the above listed *hostas* and all other cultivars known to the discoverer by the following combined traits:

1. Compact rounded-mound plant habit with dense foliage with medium green margins and lighter yellowish leaf centers;
2. Heavy-substance, stiff leaves of cordate shape and acute apex and cordate base;
3. Leaves slightly shiny surface above and below and lightly dimpled between the veins;
4. Flowers on slightly outwardly projecting scapes just above foliage with near white, broad-faced, fragrant flowers.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
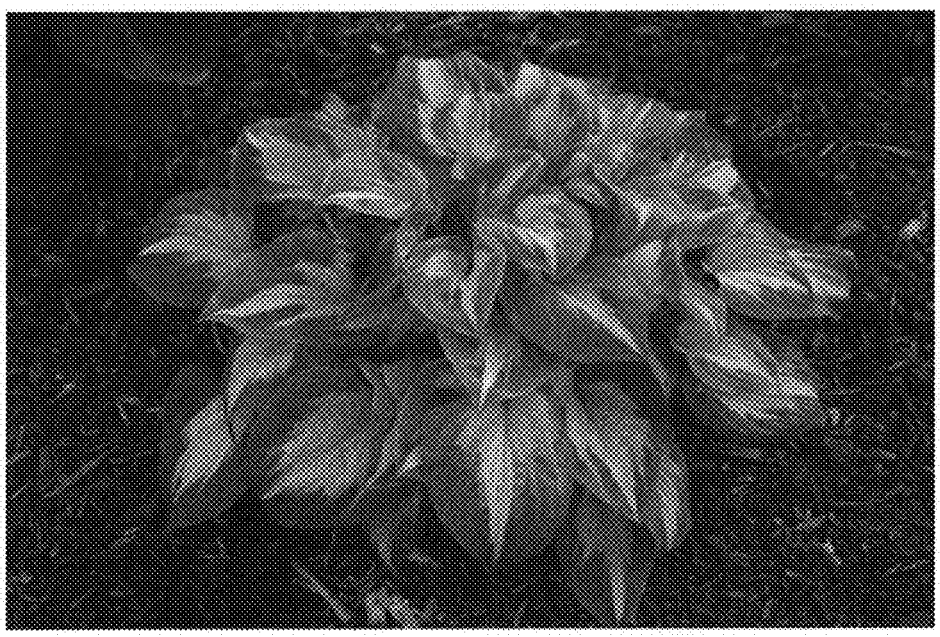
FIG. 1 shows a side view of a five-year-old plant showing the mounded plant habit.
Figure 2:
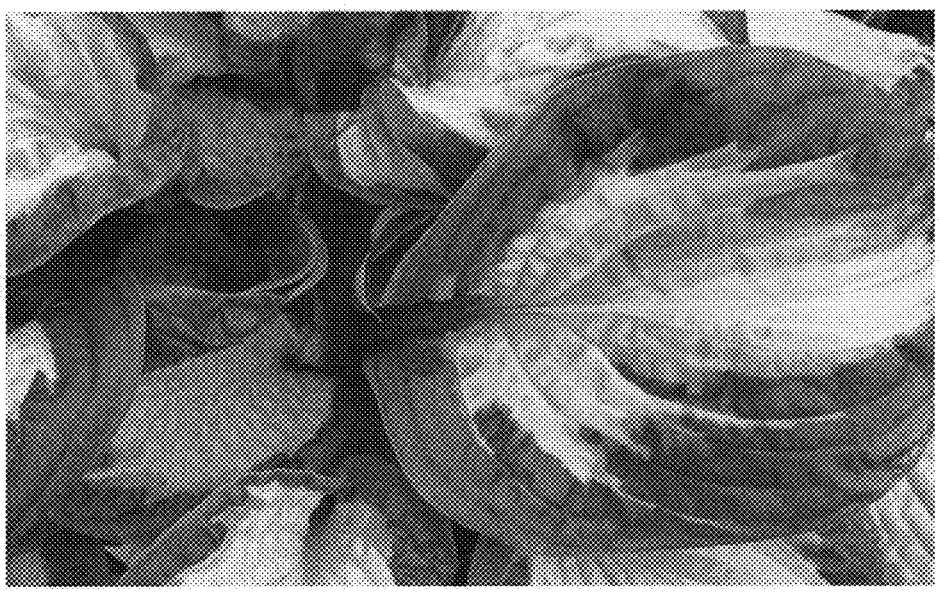
FIG. 2 shows a close-up of the foliage with variegation.

The following descriptions and color references are based on the 2015 edition of The Royal Horticultural Society Colour Chart except where common dictionary terms are used. The new plant, *Hosta* 'Etched Glass', has not been observed under all possible environments. The phenotype may vary slightly with different environmental conditions, such as temperature, light, fertility, moisture and maturity levels, but without any change in the genotype. The following observations and size descriptions are of a five-year old plant in a partially shaded trial garden and container grown plant in a greenhouse in Zeeland, Mich. with supplemental water and fertilizer.

Botanical classification: *Hosta* hybrid;

Parentage: Whole plant mutation of *Hosta* 'Stained Glass';

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155A and RHS NN155B;

Plant shape and habit: Hardy herbaceous perennial with basal rosettes of leaves emerging from rhizomes producing a short, symmetrical, rounded-mound of leaves; about 10 divisions per plant; divisions to about 3.0 cm diameter at soil level;

Plant size: Foliage height about 38.0 cm above soil line to the top of the leaves and about 81.0 cm wide at the widest point slightly above the soil line;

Foliage description: Glabrous, slightly lustrous adaxial and lustrous abaxial; cordate, with acute apex and cordate base; entire margin; with slight dimpling between the veins; blades mostly flat, without twisting; with a thicker stiffer feel than *Hosta* 'Guacamole', 'Stained Glass' and similar sports;

Leaf blade size: To about 20.3 cm long, 15.2 cm wide at base;

Leaf blade color: Early season and expanding margin adaxial nearest RHS 137A and abaxial nearest RHS 137B, adaxial center nearest RHS 151A and melded color between comprising between RHS 144A and RHS 144B, abaxial center nearest RHS N144A with melded colors between comprising RHS 144A; mid-season and later summer adaxial margin nearest RHS 137B, center a blend between RHS 4C and RHS 158A, intermediate melded colors between the center and the margin of various widths, lengths and colors comprising RHS 1B, RHS 151D and between RHS 143A and RHS 143B; mid-season and later abaxial margin nearest RHS 137A, center blend between RHS 158A and RHS 4C with intermediate melded colors between the center and margin comprising colors of a blend between RHS 146D and N144D, and a blend between RHS 151D and lighter than RHS N144D;

Petiole: Entire, glabrous, glabrous, concavo-convex; mostly straight from base of plant to leaf base with little bending or curving, strong but flexible; to about 19.0 cm long and 1.5 cm wide at base;

Petiole color: Adaxial center between RHS 145B and RHS 145A and margin between RHS 139A and RHS 139B; abaxial center nearest RHS 145A and margin nearest RHS 146B;

Veins: Parallel, lightly impressed adaxial, moderately bulging and costate on abaxial side; average about ten pairs and one main center vein;

Veins color: Adaxial midrib between RHS 145C and RHS 150C with secondary veins in margin region nearest RHS 137B and center nearest RHS 160V; abaxial midrib nearest RHS 145C and secondary veins nearest RHS 137A in margin region and nearest RHS 145C in center region;

Flower description: Perfect; single; actinomorphic; flared funnelform, with tepals recurved; held outwardly to slightly drooping; persist for normal period, usually one day on plant or as cut flower;

Flower period: Scapes remain effective with flowering beginning late July for about three weeks in Michigan;

Size: About 57.0 mm long with exserted style and stamens; corolla to about 45.0 mm long and flared to about 60.0 mm across; corolla tube to about 17.0 mm long and 5.0 mm diameter toward base;

Fragrance: Sweet;

Floral bracts: Subtending individual flowers; lanceolate, narrowly acute apex, truncate clasping base, margin entire; glabrous and lustrous adaxial and abaxial; to about 38.0 mm long and 15.0 mm across, decreasing in size distally;

Bract color: Abaxial center nearest RHS 145B and 1.5 mm wide margin nearest RHS 143A, adaxial center nearest RHS 145A and 1.5 mm wide margin nearest RHS 137C;

Tepals: Two sets of three;

Tepal color: Adaxial lighter than RHS 85D with veins nearest RHS 85D, abaxial blend between RHS NN155D and RHS 85D with apical tips of outer tepal set nearest RHS 138A;

Gynoecium: Single; tri-carpelled; 63.0 mm long;

*Style*.—Single; terete; arcuate upward distally; about 58.0 mm long and 1.0 mm diameter; color RHS NN155B.

*Stigma*.—Globose, micro-puberulent; about 1.5 mm across; color nearest RHS NN155A.

*Ovary*.—Oblong; lightly fluted; about 9.0 mm long and 3.0 mm diameter; color nearest RHS 145C.

Androecium:

*Filaments*.—Typically six; terete; glabrous; arcuate upward in distal portion; about 51.0 mm long and 0.7 mm diameter; color nearest RHS NN155C.

*Anthers*.—Ellipsoidal: dorsifixed, longitudinally dehiscent; about 3.0 mm long and 1.0 mm across; color nearest RHS 199D.

*Pollen*.—Smaller than 0.1 mm diameter; color nearest RHS 14A.

Flower bud: Clavate; with acute apex and fused tubular base; about 40.0 mm long in total and 13.0 mm wide in bulb portion, tube about 10.0 mm long and 4.0 mm diameter;

Flower bud color: Tube nearest RHS NN155A; bulb lighter than RHS 91D;

Pedicel: Terete, glabrous, lustrous; secund; outwardly; to about 8.0 mm long and 2.5 mm diameter;

Pedicel color: Nearest RHS N144C at base and lightening to nearest RHS 145D before corolla;

Peduncle: Terete; usually one per mature division and six per plant; slightly lustrous, glabrous; slightly outwardly and mostly straight; length about 56.0 cm long and about 8.0 mm diameter;

Peduncle color: When flowering nearest RHS 144A;

Fruit and seeds: Not yet observed;

Disease tolerance and resistance: The new plant has not shown any resistance to pests and diseases common to *hostas*. The plant grows best and shows best coloration with plenty of moisture, adequate drainage and light shade, but is able to tolerate some drought when mature. Hardiness at least from USDA zone 3 through 9, and other disease resistance is typical of that of other *hostas*.

It is claimed:

1. A new and distinct ornamental plant cultivar named *Hosta* 'Etched Glass' as herein described and illustrated.

* * * * *